(12) United States Patent
Wons et al.

(10) Patent No.: US 8,380,542 B2
(45) Date of Patent: Feb. 19, 2013

(54) SYSTEM AND METHOD FOR FACILITATING OUTCOME-BASED HEALTH CARE

(75) Inventors: Michael K. Wons, Naperville, IL (US); Andrew M. Kaboff, Vernon Hills, IL (US); Steven A. Wegner, Bartlett, IL (US)

(73) Assignee: CellTrak Technologies, Inc., Schaumburg, IL (US)

( * ) Notice: Subject to any disclaimer, the term of this patent is extended or adjusted under 35 U.S.C. 154(b) by 0 days.

(21) Appl. No.: 13/280,054

(22) Filed: Oct. 24, 2011

(65) Prior Publication Data

US 2012/0041788 A1 Feb. 16, 2012

Related U.S. Application Data

(63) Continuation-in-part of application No. 12/848,639, filed on Aug. 2, 2010, and a continuation-in-part of application No. 13/217,603, filed on Aug. 25, 2011, said application No. 12/848,639 is a continuation-in-part of application No. 11/586,325, filed on Oct. 24, 2006, now Pat. No. 8,019,622, said application No. 13/217,603 is a continuation of application No. 11/586,325, filed on Oct. 24, 2006, now Pat. No. 8,019,622.

(60) Provisional application No. 60/729,556, filed on Oct. 24, 2005, provisional application No. 61/405,993, filed on Oct. 22, 2010.

(51) Int. Cl.
  *G06Q 10/00* (2012.01)
  *G06Q 50/00* (2012.01)

(52) U.S. Cl. ............................................. 705/3; 705/2

(58) Field of Classification Search .................. 705/2–3; 600/300
See application file for complete search history.

(56) References Cited

U.S. PATENT DOCUMENTS

5,077,666 A  12/1991  Brimm et al.
(Continued)

OTHER PUBLICATIONS

Gray et al. "A Scalable Home Care System Infrastructure Supporting Domiciliary Care." Department of Computing Science and Mathematics, University of Stirling, Aug. 2007, Retrieved from the Internet: <URL: http://citeseerx.ist.psu.edu/viewdoc/download?doi=10.1.1.98.4934&rep=rep1&type=pdf>.

(Continued)

*Primary Examiner* — Luke Gilligan
(74) *Attorney, Agent, or Firm* — McDonnell Boehnen Hulbert & Berghoff LLP

(57) ABSTRACT

In an exemplary embodiment, a server receives from a communication device (i) an identifier of a patient and (ii) a login credential associated with an individual. The server makes a determination based on the login credential that the individual is authorized to access a patient record of the patient. Subsequent to making the determination, the server prepares an assessment based on the patient record, and provides the assessment to the communication device. The assessment includes a measurement. The server subsequently receives a measurement result from the communication device and updates the patient record based on the measurement result. The server prepares a care plan based on the patient record and provides the care plan to the communication device. The care plan includes a task. The server subsequently receives a task status from the communication device and updates the patient record based on the task status.

27 Claims, 4 Drawing Sheets

U.S. PATENT DOCUMENTS

| | | | |
|---|---|---|---|
| 6,377,810 | B1 | 4/2002 | Geiger et al. |
| 6,416,471 | B1 | 7/2002 | Kumar et al. |
| 6,450,956 | B1 | 9/2002 | Rappaport |
| 6,484,033 | B2 | 11/2002 | Murray |
| 6,741,933 | B1 | 5/2004 | Glass |
| 6,865,482 | B2 | 3/2005 | Hull |
| 6,922,566 | B2 | 7/2005 | Puranik et al. |
| 6,941,349 | B2 | 9/2005 | Godfrey et al. |
| 6,980,958 | B1 | 12/2005 | Surwit et al. |
| 7,197,467 | B2 | 3/2007 | Labadie |
| 7,259,668 | B2 | 8/2007 | Casey |
| 7,260,480 | B1 | 8/2007 | Brown et al. |
| 7,301,451 | B2 | 11/2007 | Hastings |
| 7,382,247 | B2 | 6/2008 | Welch et al. |
| 7,436,311 | B2 | 10/2008 | Rapaport et al. |
| 7,685,026 | B1 | 3/2010 | McGrady et al. |
| 8,019,622 | B2 | 9/2011 | Kaboff et al. |
| 2002/0165759 | A1 | 11/2002 | Gruber et al. |
| 2003/0028399 | A1 | 2/2003 | Davis et al. |
| 2003/0036683 | A1 | 2/2003 | Kehr et al. |
| 2004/0014423 | A1 | 1/2004 | Croome et al. |
| 2004/0172301 | A1 | 9/2004 | Mihai et al. |
| 2004/0260577 | A1 | 12/2004 | Dahlin et al. |
| 2005/0086072 | A1 | 4/2005 | Fox et al. |
| 2005/0108049 | A1* | 5/2005 | Ram et al. .................. 705/2 |
| 2005/0131740 | A1 | 6/2005 | Massenzio et al. |
| 2005/0222873 | A1 | 10/2005 | Nephin et al. |
| 2006/0004609 | A1* | 1/2006 | Kenneth et al. ............. 705/3 |
| 2006/0064320 | A1 | 3/2006 | Postrel |
| 2006/0111955 | A1 | 5/2006 | Winter et al. |
| 2006/0154642 | A1* | 7/2006 | Scannell, Jr. ............. 455/404.1 |
| 2006/0161457 | A1 | 7/2006 | Rapaport et al. |
| 2007/0156032 | A1* | 7/2007 | Gordon et al. ............. 600/300 |
| 2007/0192133 | A1 | 8/2007 | Morgan |
| 2008/0004904 | A1 | 1/2008 | Tran |
| 2008/0033750 | A1 | 2/2008 | Burriss et al. |
| 2008/0040151 | A1 | 2/2008 | Moore |
| 2008/0058615 | A1 | 3/2008 | Clapp et al. |
| 2008/0125959 | A1 | 5/2008 | Doherty et al. |
| 2009/0030731 | A1 | 1/2009 | Reiner |
| 2010/0030578 | A1 | 2/2010 | Siddique et al. |
| 2010/0114941 | A1 | 5/2010 | Von Kaenel et al. |

OTHER PUBLICATIONS

Driver et al. "Facilitating Dynamic Schedules for Healthcare Professionals.", 2007, Retrieved from the Internet: <URL: http://www.tara.tcd.ie/bitstream/2262/16486/1/04205143.pdf>.

Jianyu (Jack) Zhou. "Empirical Tracking and Analysis of the Dynamics in Activity Scheduling and Schedule Execution." University of California, Santa Barbara, Sep. 2006, Retrieved from the Internet: <URL: http://uctc.net/research/diss120.pdf>.

David Krebs. "Wireless Home Care Solutions: Addressing the Quality of Service and Performance Gap." Aug. 2007. Retrieved from the Internet: <UREL: http://na.blackberry.com/eng/campaign/healthcarecampaign/VDC%20wireless%20home%20care%20report.pdf>.

"Home Healthcare Agency Increase Field Accountability with CellTrak and Sprint." 2009 Sprint. Retrieved from the Internet: <URL: http://www.celltrak.com/chca.pdf>.

Breakthrough Tools to Increase Aide Performance Thonberry LTD. Retrieved from Internet 2010. <URL: http://www.thornberryltd.com/index.php?pID=73>.

Final Official Action mailed Dec. 8, 2011 in U.S. Appl. No. 11/586,325, 11 pages.

Claim Amendments after Final Official Action, 5 pages.

Notice of Allowance with Examiner's reasons for Allowance mailed Oct. 11, 2011 in U.S. Appl. No. 11/586,325, 7 pages.

Brochure with particulars on PROCURA scheduling software, 11 pages.

PROCURA Press Release May 10, 2000—Bayshore HealthCare, 1 page.

PROCURA Press Release Jan. 20, 2003—Brandon Regional Health Authority, 1 page.

White Paper Released regarding decision to close ParaMed Home Health Care division of Extendicare as of Mar. 31, 2003, 4 pages.

PROCURA Press Release Oct. 17, 2003—Robertson Brown Health Services, 1 page.

PROCURA Press Release Jun. 7, 2005, "Calgary Family Service Society Chooses Procura", 1 page.

PROCURA Press Release Dec. 23, 2005—Saint Elizabeth Health Care, 1 page.

Parker, R. G., First Nations Innuit Health Branch AdActus OutReach Handheld Trial Report Oct. 21, 2002, 74 pages.

AdActus OutReach Handheld Brochure, 2 pages.

AdActus OutReach Handheld Power Point, 22 pages.

AdActus OutReach Handheld Value Proposition Handout, 1 page.

Software Solutions 3M Home Health Systems Brochure, 2 pages.

CarePaths from 3M Home Health Systems Brochure, 2 pages.

Press Release—CarePath, 3M Introduces Care Paths Technology for Home Health Agencies, 2 pages.

Press Release—ACE, 3M Health Information Systems Introduces Advanced Compliance Edit (ACE) Software for Home Health Agencies, 2 pages.

3M Home Health, "3M Home Care Management System", 2 pages.

3M Home Health Schedule, 3M Scheduling System, 2 pages.

3M HHS—CarePaths, "Care Paths from 3M Home Health Systems", 2 pages.

3M Codefinder, "3M Codefinder Software for Home Health", 2 pages.

VNA Disease Management White Paper, VNA First Home Care Steps, 53 pages.

CareLink Pilot, MedShare and Wired Time Launch CareLink Pilot Project, 1 page.

CareLink, MedShare Automated Service Delivery Confirmation System, 1 page.

MedShare Press Release, Home health care agency management is easier, faster and more accurate with MedShare HC, 2 pages.

Versweyveld, Leslie, Telehomecare project for First Nations Communities in Canada to focus on wireless handheld technology, Virtual Medical Worlds Monthly, Toronto, Mar. 25, 2002, online article found at http://www.hoise.com/vmw/02/articles/vmw/LV-VM-04-02-34.html (3 pages).

Canadian Healthcare Technology, Apr. 2002, Feature Report: Wireless Systems in Healthcare, online issue, found at http://www.canhealth.com/apr02.html (11 pages).

User Manual, Microsoft Streets & Trips, 2002 (10 pages).

OpusTrack Brochure on Suite of Tools (1 page).

* cited by examiner

SYSTEM AND METHOD FOR FACILITATING OUTCOME-BASED HEALTH CARE

CROSS-REFERENCE TO RELATED APPLICATIONS

This application is a continuation-in-part of (i) application Ser. No. 12/848,639, filed on Aug. 2, 2010, and (ii) application Ser. No. 13/217,603, filed on Aug. 25, 2011, and also claims the benefit of provision Application No. 61/405,993, filed on Oct. 22, 2011. Application Ser. No. 12/848,639 is a continuation-in-part of application Ser. No. 11/586,325, filed on Oct. 24, 2006. Application Ser. No. 13/217,603 is a continuation of application Ser. No. 11/586,325, filed on Oct. 24, 2006. Application Ser. No. 11/586,325 claims the benefit of provisional Application No. 60/729,556, filed on Oct. 24, 2005. The entire contents of each application (including any source code appendix) are incorporated herein by reference.

BACKGROUND

Homecare encompasses a wide range of community-based services that support a person in need of care. This type of care may be particularly appropriate for an individual who is more comfortable receiving care in the comfort of his or her own home or a common facility. Homecare continues to be a preferred care-delivery method and is an increasingly crucial component of the healthcare system. The benefits of homecare continue to be realized on a daily basis and, as the population ages, the ability to provide high-quality care to a large population of individuals is becoming a necessity.

SUMMARY

Substantial research demonstrates that nurses can influence patient outcomes in the area of homecare. Outcome-based care systems help coordinate the gathering of (i) initial patient assessments, (ii) patient reassessments, and (iii) discharge assessments, all using common measurements, including those defined by the HOBIC and OASIS standards. HOBIC is the acronym for Health Outcomes for Better Information and Care, an initiative of the Ministry of Health and Long-Term Care in Ontario, and OASIS is the acronym for Outcome and Assessment Information Set, used primarily in the United States. The objective of these programs is to introduce a short set of standardized measures of patient status into nurses' admission and discharge assessments.

Electronic assessments can be built into nurses' usual activities. Such assessments may include initial patient assessments, patient reassessments, and discharge assessments. With these assessments, nurses can assess their patients' statuses throughout the homecare process, compare their patients with others of similar age, gender and diagnosis, determine when patients are achieving their best outcomes, and know when patients are sufficiently prepared to care for themselves after discharge. The assessment data, when gathered in a common way and shared across a care team, helps to provide the data necessary to adjust care plans and to provide for the best care possible in the future.

In an exemplary embodiment of the invention, a server receives from a communication device (i) an identifier of a patient and (ii) a login credential associated with an individual. The individual is selected from among a plurality of individuals that includes a physician and a family member of the patient. The server then makes a determination based on the login credential that the individual is authorized to access a patient record of the patient. The patient record is stored in a database and is associated with the patient identifier.

Subsequent to making the determination, the server prepares an assessment based on the patient record, and provides the assessment to the communication device. The assessment includes a measurement to be taken (such as the patient's blood pressure, heart rate, wound condition, etc.). The server subsequently receives a measurement result from the communication device and updates the patient record based on the measurement result. The measurement result (such as the heart rate, blood pressure, or wound condition) is associated with the measurement.

The server prepares a care plan based on the patient record (which reflects the received measurement result) and provides the care plan to the communication device. The care plan includes a task to be performed (such as providing blood-pressure medication, etc.). The server subsequently receives a task status from the communication device and updates the patient record based on the task status. The task status (such as a confirmation that the medication was administered) is associated with the task.

Previously, assessments were paper based and were available only to a single care-giving individual until the results were manually entered into a clinical system. The error rate associated with paper-based manual processes may be as high as 10%. Paper-based forms are also susceptible to errors that arise from poor handwriting, missing pages, or unreadable data, any of which could require a caregiver to completely redo an assessment.

With the embodiments described herein, caregivers and the entire care team can see the results of assessments in real-time and make changes to the care plan provided to the patient. A care plan can be changed just as quickly as assessment results are gathered. The care team no longer needs to wait for information to be manually entered into a system because this process has been eliminated (along with the errors that may occur in paper-based processes).

Further, the embodiments described herein bring together the care team with simultaneous access to electronic health records data. Hospitals, care centers, doctors, home and community care providers, community care access centers, insurance payors, government health systems, family members, and trusted advisors can all access a patient's health record, simultaneously and in real-time. The care team may also be able to access other records of the patient, such as a personal healthcare record that is owned and maintained by the patient.

The embodiments described herein may be part of an integrated home health point-of-care mobility and administration system that enables efficiencies with scheduling, staff management, time and attendance, GPS and directions, and delivering a patient specific care plan at the point-of-care.

DETAILED DESCRIPTION OF THE DRAWINGS

Figure 1:
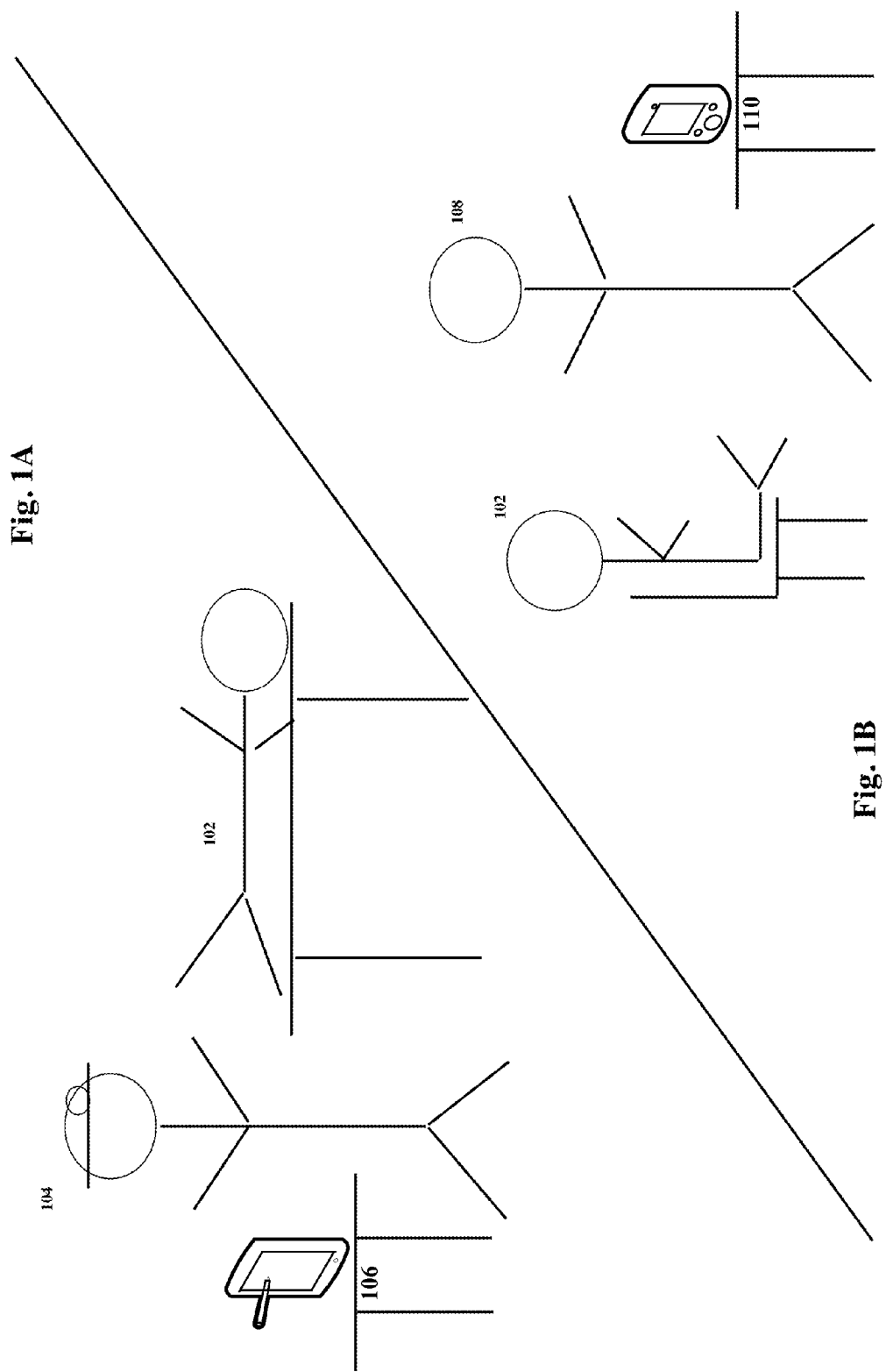
FIGS. 1A and 1B are simplified depictions of a care system.

FIGS. 1A and 1B are simplified depictions of a care system. FIG. 1A depicts patient 102 with physician 104 and computer 106. The patient may be visiting physician 104 for the first time, or may be visiting for a follow-up or subsequent appointment. In either case, the physician may want to assess the current status of the patient. For example, the physician may want to obtain a heart rate, blood pressure, and temperature of the patient. The physician may also want to check the status of a previously performed surgical suture. Those having skill in the art will recognize that a patient's current status may include other patient vitals and conditions.

Computer 106 may aid in the physician's assessment. For example, the computer may present a list of standard vitals and conditions that must or should be assessed during every visit with the physician. The computer could also present different vitals depending on whether this is a first or subsequent visit of the patient. As shown, the computer could take the form of a mobile device such as a tablet computer or smartphone, among numerous other examples.

Computer 106 may be able to communicate with a server (perhaps connected via the Internet) to download measurements to be taken for an assessment, the results of previous assessments, and/or the tasks to be performed for a care plan, among numerous other examples. The computer may also be able to upload a new assessment generated by the physician (including new tasks to be performed), the results of a just-performed assessment, and/or the status of a just-performed care plan, among other examples.

Physician 104 could enter the results of the assessment into computer 106. For example, the computer could present a text input next to each measurement (e.g., a heart rate and a blood pressure) of an assessment. The physician could enter the results of those measurements into the computer in the associated text inputs. As another possibility, the physician could upload visual media (such as a picture or video) or audio media (such as a sound recording. Alternatively, the physician 104 could enter results via voice recognition software resident on the computer 106. Those having skill in the art will recognize that the result of the measurement could take numerous other forms as well.

Following the assessment of patient 102, physician 104 may want to provide care based on the assessment. Computer 106 may also aid in the development and execution of a patient care plan. For example, the computer 106 could automatically generate the care plan based on the physician's assessment. If the assessment determined that the patient had a high blood pressure, the computer 106 could generate a care plan with tasks designed to lower the patient's blood pressure. As another possibility, physician 104 could develop part or all of the care plan (perhaps based on the assessment), and store the care plan in computer 106.

Once the care plan is generated, the computer 106 could present to physician 104 individual tasks associated with the care plan. Computer 106 could present a checkbox next to each task item. The physician 104 could use an input device of computer 106 to check the checkbox, thus indicating that the particular task has been performed. For example, if the assessment determined that the patient had a high blood pressure, the care plan might include the task of administering a blood-pressure medication. Upon administering the medication, the physician could check the checkbox next to this presented task item.

Further, after a previously-generated assessment is performed, a new assessment may be generated. The assessment could be generated completely by computer 106 (or by a server connected to computer 106), and/or could be generated partially or completely by physician 104 or another caregiver (such as a nurse or family member). The physician, after generating a new assessment, could upload the generated assessment via computer 106 for subsequent use by physician 104, family member 108, a nurse, or another individual or entity.

FIG. 1B depicts patient 102 with family member 108 and computer 110. Family member 108 may perform assessments and execute care plans before and/or after a visit with physician 104. For example, physician 104 may develop a care plan and store that care plan in computer 106. Family member 108 may use computer 110 to retrieve that stored care plan and perform (or assist in performing) the various tasks associated with that care plan.

In an embodiment, family member 108 is an individual within patient 102's nuclear (or "immediate") family, such as a son, daughter, brother, sister, mother, or father, as examples. In another embodiment, family member 108 is within the patient's extended family, such as a grandson, granddaughter, cousin, grandmother, or grandfather. Other examples are possible as well. For example, family member 108 could be an individual that isn't related by law or blood to patient 102, but is still identified as being a family member. Such an individual could be a close friend and/or domestic worker, among other possibilities.

Family member 108 may also use computer 110 (which could also be a mobile device, among other possibilities) to perform assessments. For example, after one or more days of care by family member 108, the family member may perform an assessment with the aid of computer 110 to determine the results of the current care plan. The family member may perform the assessment based on a list of tests to perform presented by the computer, and enter the results into the computer.

Physician 104 and/or the server (among other examples) may then be able to generate a new care plan based on the assessments performed by family member 108. For example, after the family member has performed one or more assessments and entered the results into computer 110, physician 104 may be able to use computer 106 to view the results of the assessment and modify the care plan. If the blood pressure of patient 102 has dropped, physician 104 may alter the care plan to require administration of a smaller dosage of blood-pressure medication. Note that physician 104 could make these changes to the care plan even without a subsequent visit to physician 104 by patient 102.

Figure 2:
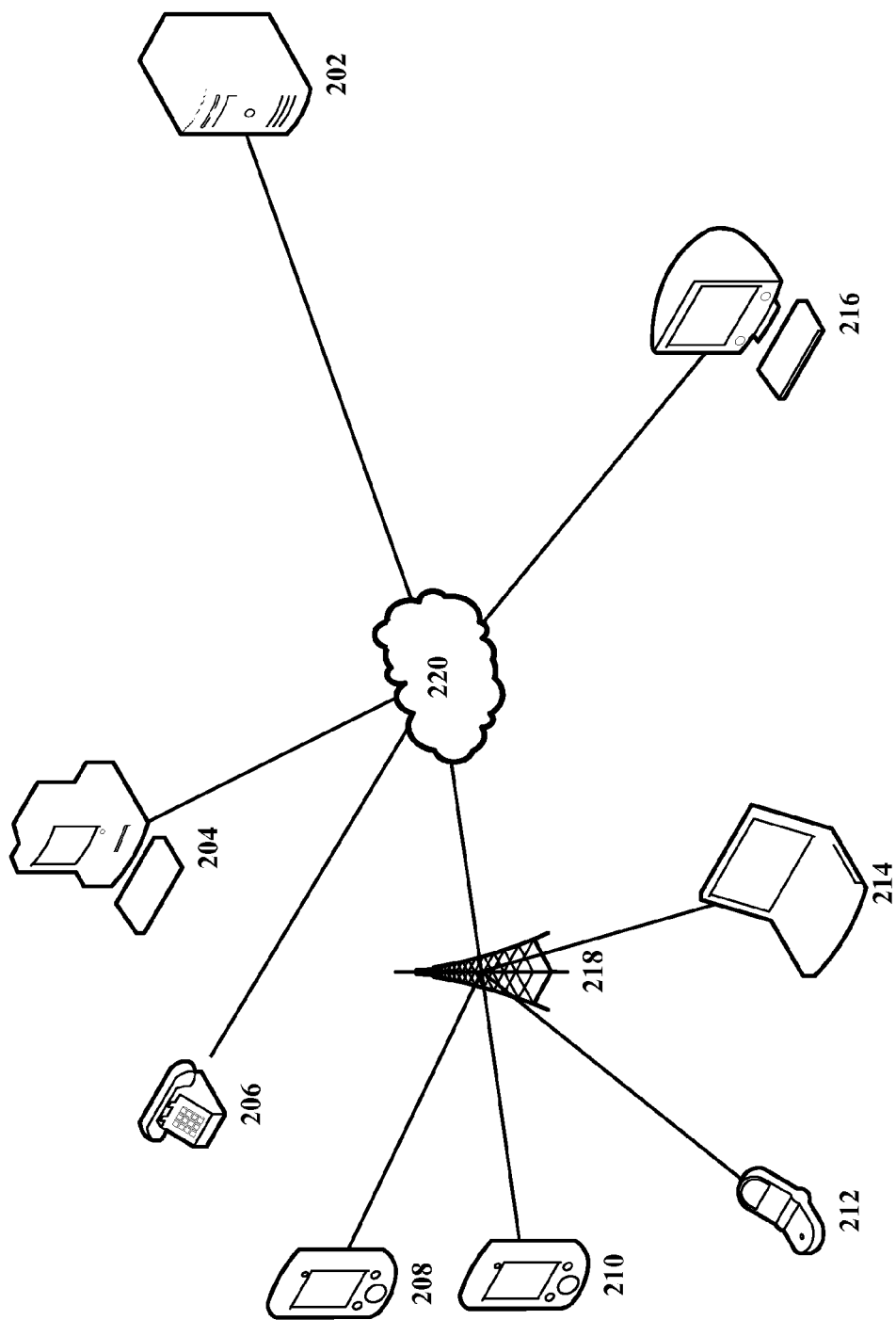
FIG. 2 is a diagram of a communication system, in accordance with exemplary embodiments.

FIG. 2 is a diagram of a communication system. It should be understood that this and other arrangements described herein are set forth only as examples. Those skilled in the art will appreciate that other arrangements and elements (e.g., machines, interfaces, functions, orders, and groupings of functions, etc.) can be used instead, and that some elements may be omitted altogether. Further, many of the elements described herein are functional entities that may be implemented as discrete or distributed components or in conjunction with other components, and in any suitable combination and location. Various functions described herein as being performed by one or more entities may be carried out by hardware, firmware, and/or software. Various functions may be carried out by a processor executing instructions stored in memory.

As shown in FIG. 2, a communication system 200 may include server 202, personal computers 204, 214, and 216, telephone 206, smartphones 208 and 210, and feature phone 212, all of which may be communicatively connected via gateway 218 and/or network 220. Additional entities could be present, such as additional communication devices in communication with network 220 (perhaps via gateway 218), additional gateways, additional servers, etc. Also, there could be one or more devices and/or networks making up at least part of one or more communication links. It should further be understood that not all entities depicted in FIG. 2 need to be present.

Server 202 may be any device capable of carrying out the server functions described herein. The server could be an individual server machine, a group of server machines, and/or a virtual server that is hosted on one or more physical machines with other virtual servers. Server 202 could take the form of server system 104 described in U.S. Patent Application Publication No. US 2011-0010087 A1, the entire contents of which are incorporated by reference.

Server 202 could include a processor, a data storage, and/or a communication interface, or any combination of these. The data storage could take the form of a hard disk drive, a random-access memory, a read-only memory, an application-specific integrated circuit (ASIC), a CD-ROM drive, and/or a universal serial bus (USB) flash drive, among other examples. The data storage could include machine-language instructions for performing the server-related tasks described herein, and/or could store a database of patient records, assessments, care plans, and related information, among other possibilities. The communication interface could facilitate communication between server 202 and another entity, such as devices 204-216. As such, the communication device could take the form of an Ethernet adapter, among other possibilities.

In an embodiment, the server functions described herein are carried out by a software or hardware module that is part of a base and mobile framework (such as framework 302 described in U.S. Patent Application Publication No. US 2011-0010087 A1). Other modules within the framework could provide point-of-care scheduling of caregivers, electronic visit record functionality, GPS tracking and management of caregivers, and interactive voice response functionality, among numerous other possibilities.

It should also be understood that the server-functions described herein could take the form of machine-language instructions stored on a non-transitory computer-readable medium. The medium could take the form of a device similar to that of the above-described data storage. The instructions, if executed by a processor of a computer, could cause the computer to perform the server functions represented by the machine-language instructions.

In an exemplary embodiment, server 202 includes a database (such as a relational database management system or RDBMS). The database could store a number of tables, with each table including one or more columns and rows. In an embodiment, the data of every row in a particular column represents a particular data type (such as a number or a date), and each row represents an entry of (potentially) related information. The database could be stored in the data storage, or could be accessible via the communication interface, among other possibilities.

In another embodiment, the information stored by server 202 is protected by one or more security measures. For example, communication between server 202 and devices 204-216 may be encrypted and/or obfuscated using Transport Layer Security (TLS) or Secure Sockets Layer (SSL), among numerous other examples. Further, server 202 may stored patient-related information in an encrypted form and may only decrypt that information upon receiving proper login credentials from physician 104, family member 108, or another member of the care team for patient 102, among numerous other possibilities.

Devices 204-216 may be generally referred to as communication devices, and may be any devices capable of performing the communication-device functions described herein. For example, devices 204-216 may take the form of communication device 101 described in U.S. Patent Application Publication No. US 2011-0010087 A1.

Particularly, telephone 206 may be any device capable of communicating via the public switched telephone network (PSTN). As such, telephone 206 may be capable of communicating via the plain old telephone system (POTS), using full duplex over two-wire circuits and dual-tone multi-frequency (DTMF) signaling via a circuit-switched network, for example. As another possibility, telephone 206 may be configured to communicate over the PSTN using a cellular or Internet connection via a packet-switched network (such as VoIP using the Internet). Telephone 206 may include a number of physical or virtual keys, perhaps arranged in a standard 4×3 grid.

Wireless telephones 208-212 may also be capable of communicating via the PSTN. In addition, these phones may include components, similar to those in server 202, that allow the phones to execute various computer applications. These applications could communicate with other devices and/or server 202 via the PSTN and or a packet-switched network such as the Internet, among other possibilities.

Gateway 218 may be, for example, any device capable of facilitating wireless communication with devices 208-214. Accordingly, gateway 218 may take the form of a Wi-Fi access point and/or a base station of a cellular (mobile) phone network, among other possibilities.

Network 220 may be any network capable of facilitating communication between one or more of devices 204-216. As such, network 220 could take the form of the Internet and/or the public switched telephone network, among other examples.

Figure 3:
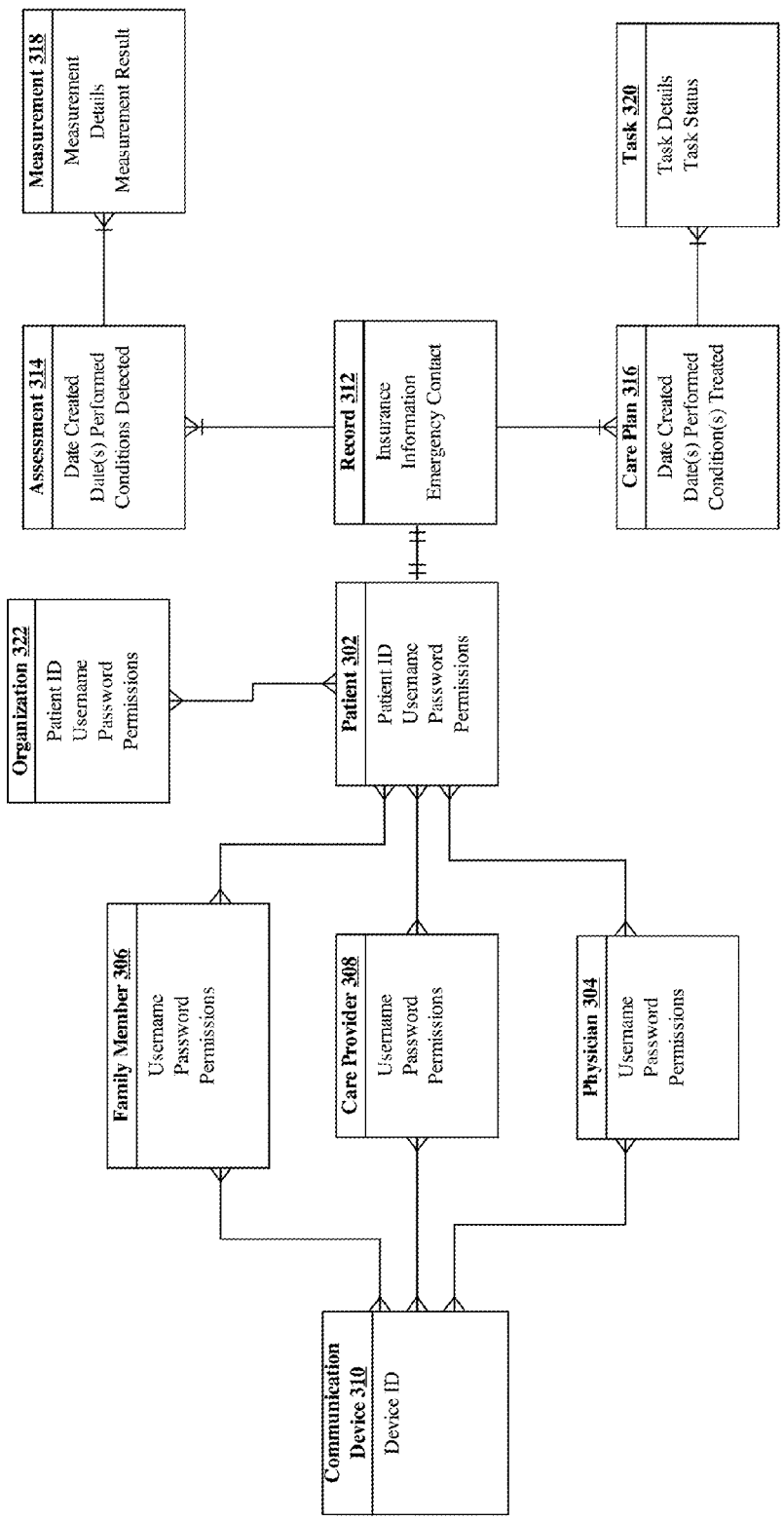
FIG. 3 is an entity relationship diagram, in accordance with exemplary embodiments.

FIG. 3 is an entity relationship diagram, in accordance with exemplary embodiments. As shown, system 300 includes patient 302, physician 304, family member 306, care provider 308, communication device 310, patient record 312, assessment 314, care plan 316, measurement 318, and task 320. The relationships between each entity 302-320 are represented using Crow's Foot notation.

It should be understood that part or all of the information and/or relationships depicted in FIG. 3 may be stored electronically. For example, the various entities depicted in system 300 may be stored in a RDBMS. As another possibility, the entities could be stored using a flat-file representation such as a comma-separated values (CSV) file, an XML file, and/or a human-readable ASCII file, among other examples. Further, the information and relationships, whether stored in an RDBMS or otherwise, may be stored in a secure form using encryption and obfuscation, among other possibilities. Access to the RDBMS or other data-storage system may require a username and password and/or a certificate, as examples.

It should also be understood that the various entities depicted in FIG. 3 may represent non-electronic information. For example, each physician 304 may represent a living individual, and patient record 312 may represent a paper file. The remainder of the specification assumes that all entities depicted in FIG. 3 represent electronic versions (e.g., electronic patient records) of those entities.

It should also be understood that additional entities, relationships, and data associated with each entity and relationship may also be present. For example, each entity that is stored in a database could also be associated with a primary key that uniquely identifies each instance of the entity. As another example, other entities could be present to map the many-to-many (or other) relationships between the various entities depicted in FIG. 3.

As shown in FIG. 3, each patient 302 is associated with at least one physician 304 and at least one family member 306. Each patient may also be optionally associated with one or more other care providers 308, such as another physician, a friend, and/or a trusted advisor, among other examples. Further, each physician, family member, and care provider may be associated with one or more patients.

In an embodiment, each physician, family member, and/or care provider is able to access patient records of only those patients to which they have been assigned. For example, Martha Washington may be allowed to access the patient record of her husband George Washington after the appropriate relationship between Martha (as family member) and George (as patient) has been established in the database. However, Martha would not be able to access the patient record of John Adams without an established relationship between Martha (as family member) and John (as patient). This relationship could be configured by John, John's physician, and/or another member of John's care team, among numerous other examples.

Each physician 304, family member 306, and care provider 308 may have one or more associated communication devices 310. The communication devices may be any devices that allow access to part or all of patient record 312, and may take the form of any of communication devices 204-216, as examples. Further, each communication device 310 may be associated with multiple entities (such as multiple physicians, family members, care providers, or any combination of these). For example, both a physician and a family member may be able to access patient record 312 via the same personal computer or mobile device installed at a hospital or other care center.

Each physician 304, family member 306, and care provider 308 may be associated with one or more login credentials. For example, each of these entities may have an associated username and password. These entities may be able to access patient record 312 via communication device 310 after providing the associated username as password. Those having skill in the art will recognize that other types of login credentials may be used as well (or instead), such as a private cryptographic key, as USB token, and/or a biometric scanner, among other examples. Further, different types of login credentials could be used based on the entities' ability to access and/or modify patient record 312.

In an embodiment, physician 304 is able to modify the relationships between patient 302 and family member 306, care provider 308, as well as physician 304. For example, the physician may be able to assign himself or herself to a patient, thus creating the relationship. The physician may then be able to assign one or more family members to the patient after ensuring that the family member is competent to provide patient assessment and/or care, for example. In other embodiments, family member 306 and care provider 308 are able to modify these relationships. Those having skill in the art will recognize that any entity may be given full or restricted access to modify these relationships, and that other entities not shown (such as a server administrator) may be able to modify these relationships as well.

In an embodiment, each patient also has an associated login credential, and may have limited or full access to read and/or modify patient record 312 and/or the relationships between the patient and physician 304, family member 306, and/or care provider 308. For example, physician 304 may decide that patient 302 should be allowed to associate with additional family members 306, and so physician 304 may allow patient 302 to establish these relationships. However, the physician may not want to provide the patient with the ability to change a care plan 316 of the patient. The physician may be able to set the permissions of patient 302 to be able modify certain relationships, but not to modify other aspects of patient record 312 (as an example).

Note that, while patient 302, physician 304, family member 306, and care provider 308 are shown as separate entities, those having skill in the art will recognize that these individuals may be represented in server 302 as generic users, each with an associated role (e.g., patient, physician, family member, care provider, etc.) and permissions to make changes to the patient record (and associated text, video, audio, and other data stored with the patient record) as well as the relationships between the patient and other individuals.

In an embodiment, each patient is associated with one patient record (and each patient record is associated with one patient). Patient record 312 may store various information regarding the treatment of patient 302, such as illness and treatment history, as well as contact and insurance information, as examples. Further, patient record 312 may be associated with one or more patient assessments 314 and one or more patient care plans 316.

Each patient assessment 314 may store a date that the assessment was created, a date (or dates) that the assessment was performed, and/or a condition detected by the assessment, as examples. Each assessment may have one or more associated measurements 318 that are taken as part of the assessment. Each measurement could store user-readable details of the measurement (such as "take blood pressure using automatic blood pressure monitor") along with a measurement result (such as "190/115").

Similarly, each patient care plan 316 may store a date that the care plan was created, a date (or dates) that the care plan was performed, and/or a condition treated by the care plan, as examples. Each care plan may have one or more associated tasks 320 that are performed as part of the care plan. Each task could store user-readable details of the task (such as "administer blood-pressure medication") along with a task status (such as "medication administered").

Health organization 322 may be able to access part or all of patient record 302, in addition to other patient records stored by the organization. The organization may use these patient records to determine which care plans led to positive patient outcomes (perhaps as measured by the assessments), as described more fully below. Further, more than one organization may be able to access patient record 302 (and other patient records). The health organization could be a government agency, an insurance provider, and/or another entity servicing a large number of patients, to name just a few examples.

Figure 4:
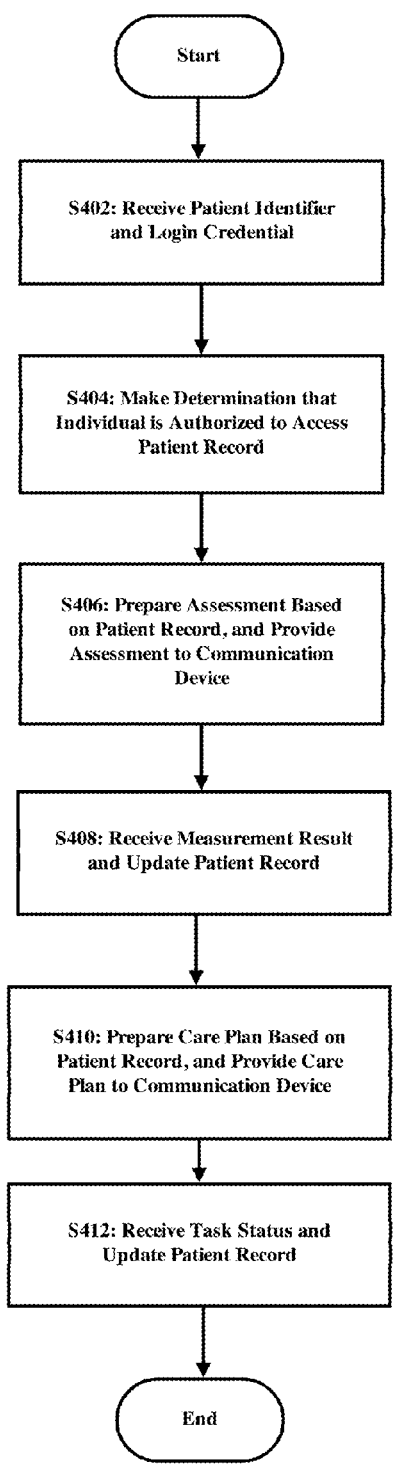
FIG. 4 is a diagram of a flowchart, in accordance with exemplary embodiments.

FIG. 4 is a diagram of a flowchart, in accordance with an exemplary embodiment. As shown in FIG. 4, method 400 begins at step 402, with server 202 receiving from communication device 310 an identifier of a patient and a login credential.

In an embodiment, the login credential is associated with an individual from a care team comprising a plurality of individuals authorized to access a patient record of the patient. The plurality of individuals may include, for example, a physician and a family member of the patient. For example, every individual among the plurality of individuals may be authorized to access the patient record upon providing a login credential via the communication device (and after the server determines that the individual is authorized to access a patient record based on the login credential). However, it should be understood that the received login credential need not actually be associated with the physician or family member.

Further, the plurality of individuals may contain more than one physician and/or family member. The plurality may also contain other individuals, such as trusted advisors, friends, and insurance payors, among numerous other examples. It should also be understood that the plurality of individuals authorized to access a patient record need not include a physician and a family member. In other embodiments, that plurality could include just a physician, just a family member, just a care provider, or perhaps another individual, or any combination of these, among other possibilities.

At step 404, server 202 makes a determination based on the login credential that the individual is authorized to access the patient record. The determination could include server 202 checking a database to determine that an appropriate relationship exists between the individual and the patient. The relationship could be represented by an entry in a table in an RDBMS indicating that the individual is associated with the patient, and/or could be represented by a CSV or XML file, among other possibilities. For example, the entry could indicate an association between the username of the login credential on the one hand and the identifier of the patient on the other. Those having skill in the art will recognize that other means for making this determination are possible without departing from the scope of the claims.

Step 404 could also include server 202 decrypting information associated with a patient record. For example, the login credentials could be used to decrypt the information. In an exemplary embodiment, the patient record is stored using the Advanced Encryption Standard (AES), and the record is decrypted using the login credentials (which could include a password), perhaps in combination with a decryption key.

At step 406, server 202 prepares an assessment based on the patient record, and provides the assessment to the communication device. The assessment could be a standard assessment in accordance with HOBIC, OASIS, or another standard, as discussed above. Similarly, each measurement in the assessment could represent a standard measurement in accordance with a standard. The assessment could include any number of measurements.

Preparing the assessment could include server 202 creating a new instance of assessment 314, and creating one or more measurements 318. Relatedly, providing the assessment 314 to the communication device could include sending an electronic representation of the assessment (perhaps using Extensible Markup Language (XML) or another format) to the communication device. The communication device could then present the assessment, along with each individual measurement, to the user of the communication device, perhaps as described above with reference to FIG. 1.

At step 408, server 202 receives a measurement result from the communication device, and updates the patient record based on the measurement result. Receiving the measurement result could include receiving an XML representation of the measurement result. It should be understood that the communication device could (and likely will) provide more than one measurement result to the server.

Updating the patient record with the measurement result could include server 202 updating a measurement result field for each associated measurement 318. For example, if at step 406 server 202 creates a measurement 318 with measurement details that include "take blood pressure," server 202 at step 408 could find this measurement 318 and update the measurement result with that received from the communication device (e.g., "190/115").

At step 410, server 202 prepares a care plan based on the patient record, and provides the care plan to the communication device. Preparing the care plan could include server 202 creating a new instance of care plan 316, and creating one or more tasks. Providing care plan 316 to the communication device could include sending an XML (or other) representation of the care plan to the device. As another possibility, providing the care plan (or assessment) could include sending a text message, a voice message, and/or an HTML file, among numerous other possibilities. The communication device could then present the care plan, along with each individual task, to the user of the communication device.

At step 412, server 202 receives a task status from the communication device, and updates the patient record based on the task status. Updating the patient record with the task status could include server 202 updating a task status field for each associated task 320. For example, if at step 410 server 202 creates a task 320 with task details that include "administer blood pressure medication," server 202 at step 412 could find this task 320 and update the task status with that received from the communication device (e.g., "medication administered").

Steps 402-410 (or any combination of these steps) may be repeated as necessary to provide optimal outcomes for patients. For example, after providing an initial patient assessment and a first care plan to the communication device, server 202 could prepare a patient reassessment and a second care plan, and provide these to the communication device. This process culminates with a patient discharge assessment (with or without a subsequent care plan).

Further, the assessments and care plans collected at steps 402-410 may be provided to a health organization (such as health organization 322). In an embodiment, organization 322 uses assessments and care plans collected from a plurality of patients to determine which care plans resulted in a positive outcome for the patient (such as patient discharge, a cure of a condition, etc.), and which care plans did not improve the patient's condition (or perhaps worsened the condition).

Further, health organization 322 may look for any correlation between outcomes, care plans, and patient demographics. For example, the health organization may use the collected care plans and assessments to determine that a certain care plan improved a certain condition (such as heart disease) better in women than in men. The organization might determine that another care plan better improved the certain condition in men. Accordingly, server 202 and/or the patient's care team could use this information to create a care plan that is more likely to lead to a successful outcome for patient 302. Other demographics (such as age, weight, race, etc.) could be used as well without departing from the scope of the claims.

Various embodiments described herein allow an intelligent assessment of a patient's condition at the point-of-care. For example, an initial or subsequent assessment may be based upon a previous or standard assessment that is both (i) tailored for an individual patient while also (ii) known to accurately assess a patient's condition and determine a proper care plan. As another example, electronic-based data entry may reduce input errors associated with paper-based assessments, while also providing instant access to the assessment data for other care team members.

Further, various embodiments allow (i) patient-specific and (ii) positive-outcome oriented care plans. That is, a care plan may be chosen for a patient (i) based on other care plans for other patients with similar conditions, demographics, etc., but also (ii) based on the patient's specific needs (perhaps as determined by the assessments).

Further still, numerous embodiments described herein allow the assessments and care plans to be shared within a health organization, and with other health organizations.

Sharing patient records allows a greater sample size, which may better facilitate the determination of correlations between care plans and positive outcomes. Part or all of the patient record (including assessments and care plans) may be shared, perhaps with appropriate security to prevent other organizations from misusing the information and/or personally identifying individual patients, for example. In an embodiment, patient names and street addresses are removed from shared patient records.

It should be understood that the illustrated embodiments are examples only and should not be taken as limiting the scope of the present invention. The claims should not be read as limited to the described order or elements unless stated to that effect. Therefore, all embodiments that come within the scope and spirit of the following claims and equivalents thereto are claimed as the invention.

The invention claimed is:

1. A method carried out by a server, the server comprising a communication interface, a processor, and a data storage comprising instructions that, if executed by the processor, cause the server to carry out the steps comprising:
   receiving from a communication device (i) an identifier of a patient and (ii) a login credential associated with an individual from a care team comprising a plurality of individuals authorized to access a patient record of the patient, wherein the plurality of individuals comprises a physician, a nurse, and a family member of the patient, wherein the physician, the nurse, and the family member of the patient are individuals other than the patient;
   making a determination based on the login credential that the individual is authorized to access the patient record, wherein the patient record is stored in a database and is associated with the patient identifier;
   subsequent to making the determination, preparing an assessment based on the patient record, and providing the assessment to the communication device, wherein the assessment comprises a measurement;
   receiving a measurement result from the communication device, and updating the patient record based on the measurement result, wherein the measurement result is associated with the measurement;
   preparing a care plan based on the updated patient record, a patient specific need, and a patient demographic, and providing the care plan to the communication device, wherein the care plan comprises a task;
   receiving a task status from the communication device, and updating the updated patient record based on the task status, wherein the task status is associated with the task;
   determining an outcome of the care plan based on the updated patient record, wherein the outcome is a positive outcome or a negative outcome;
   identifying a correlation between the outcome, the care plan, and the patient demographic;
   preparing a subsequent care plan based on the identified correlation, the updated patient record, the task status, the patient specific need, and a physician assessment, and providing the subsequent care plan to the communication device, wherein the subsequent care plan comprises a subsequent task;
   receiving a subsequent task status from the communication device, and adjusting the updated patient record based on the subsequent task status, wherein the subsequent task status is associated with the subsequent task; and
   preparing a discharge assessment based on the adjusted patient record, and providing the discharge assessment to the communication device.

2. The method of claim 1, further comprising:
   after preparing the care plan, preparing a subsequent assessment based on the patient record, and providing the subsequent assessment to the communication device, wherein the subsequent assessment comprises a subsequent measurement; and
   receiving a subsequent measurement result from the communication device, and updating the patient record based on the subsequent measurement result, wherein the subsequent measurement result is associated with the subsequent measurement.

3. The method of claim 1, wherein the communication device is a device selected from a group consisting of a personal computer, a telephone, a smartphone, and a feature phone.

4. The method of claim 1, wherein the login credential comprises a username and password of the individual.

5. The method of claim 1, wherein the database comprises a relational database management system.

6. The method of claim 1, wherein the database comprises a flat-file representation.

7. The method of claim 1, further comprising:
   receiving from the physician an authorization to allow the individual to access the patient record.

8. The method of claim 1, further comprising:
   receiving from the family member an authorization to allow the individual to access the patient record.

9. The method of claim 1, further comprising:
   receiving from the patient an authorization to allow the individual to access the patient record.

10. The method of claim 1, wherein identifying the correlation further comprises:
    providing a plurality of assessments and a plurality of care plans to a health organization; and
    receiving information regarding a correlation between one or more care plans and one or more positive outcomes.

11. The method of claim 10, wherein determining the outcome further comprises:
    the health organization comparing the care plans to the outcome to determine positive-outcome care plans.

12. The method of claim 1, wherein receiving the measurement result comprises receiving text, visual media, or audio media.

13. The method of claim 1, wherein the plurality of individuals further comprises the patient.

14. A system comprising:
    a server; and
    a communication device;
    wherein the server is configured to:
      receive from a communication device (i) an identifier of a patient and (ii) a login credential associated with an individual from a care team comprising a plurality of individuals authorized to access a patient record of the patient, wherein the plurality of individuals comprises a physician, a nurse, and a family member of the patient, wherein the physician, the nurse, and the family member of the patient are individuals other than the patient,
      make a determination based on the login credential that the individual is authorized to access the patient record, wherein the patient record is stored in a database and is associated with the patient identifier,
      subsequent to making the determination, prepare an assessment based on the patient record, and provide the assessment to the communication device, wherein the assessment comprises a measurement, receive a measurement result from the communication device, and update the patient record based on the measurement result, wherein the measurement result is associated with the measurement, prepare a care plan based on the updated patient record, a patient specific need, and a patient demographic, and provide the care plan to the communication device, wherein the care plan comprises a task, and receive a task status from the communication device, and update the updated patient record based on the task status, wherein the task status is associated with the task, determine an outcome of the care plan based on the updated patient record, wherein the outcome is a positive outcome or a negative outcome, identify a correlation between the outcome, the care plan, and the patient demographic, prepare a subsequent care plan based on the identified correlation, the updated patient record, the task status, the patient specific need, and a physician assessment, and providing the subsequent care plan to the communication device, wherein the subsequent care plan comprises a subsequent task, receive a subsequent task status from the communication device, and adjusting the updated patient record based on the subsequent task status, wherein the subsequent task status is associated with the subsequent task, and prepare a discharge assessment based on the adjusted patient record, and providing the discharge assessment to the communication device; and wherein the communication device is configured to:

provide to the server (i) the identifier of the patient and (ii) the login credential, receive the assessment from the server, provide the measurement result to the server, receive the care plan from the server, and provide the task status to the server.

15. The system of claim 14, wherein the server is further configured to:

after preparing the care plan, prepare a subsequent assessment based on the patient record, and provide the subsequent assessment to the communication device, wherein the subsequent assessment comprises a subsequent measurement; and receive a subsequent measurement result from the communication device, and update the patient record based on the subsequent measurement result, wherein the subsequent measurement result is associated with the subsequent measurement.

16. The system of claim 14, wherein the server comprises a communication interface, a processor, and a data storage comprising instructions that, if executed by the processor, cause the server to carry out server functions.

17. The system of claim 14, wherein the communication device comprises a communication interface, a processor, and a data storage comprising instructions that, if executed by the processor, cause the communication device to carry out communication-device functions.

18. The system of claim 14, wherein the communication device is a device selected from a group consisting of a personal computer, a telephone, a smartphone, and a feature phone.

19. The system of claim 14, wherein the login credential comprises a username and password of the individual.

20. The system of claim 14, wherein the database comprises a relational database management system.

21. The system of claim 14, wherein the database comprises a flat-file representation.

22. The system of claim 14, wherein the server is further configured to:

receive from the physician an authorization to allow the individual to access the patient record.

23. The system of claim 14, wherein the server is further configured to:

receive from the family member an authorization to allow the individual to access the patient record.

24. The system of claim 14, wherein the server is further configured to:

receive from the patient an authorization to allow the individual to access the patient record.

25. The system of claim 14, wherein the server is further configured to:

provide a plurality of assessments and a plurality of care plans to a health organization; and receive information regarding a correlation between one or more care plans and one or more positive outcomes.

26. The system of claim 14, wherein the measurement result comprises text, visual media, or audio media.

27. The system of claim 14, wherein the plurality of individuals further comprises the patient.

* * * * *